(12) United States Patent
Gardiner et al.

(10) Patent No.: US 10,113,950 B2
(45) Date of Patent: Oct. 30, 2018

(54) FRICTION TESTER FOR A TRAVEL SURFACE

(71) Applicant: W.D.M. Limited, Bristol (GB)

(72) Inventors: John Leslie Gardiner, Bristol (GB); Richard Dal Lago, Bristol (GB)

(73) Assignee: W.D.M. LIMITED, Bristol (GB)

( * ) Notice: Subject to any disclaimer, the term of this patent is extended or adjusted under 35 U.S.C. 154(b) by 114 days.

(21) Appl. No.: 14/919,977

(22) Filed: Oct. 22, 2015

(65) Prior Publication Data

US 2016/0116395 A1    Apr. 28, 2016

(30) Foreign Application Priority Data

Oct. 22, 2014 (GB) .................................. 1418818.9

(51) Int. Cl.
  *G01N 3/56* (2006.01)
  *G01N 19/02* (2006.01)
  *B60T 8/172* (2006.01)
(52) U.S. Cl.
  CPC .............. *G01N 19/02* (2013.01); *B60T 8/172* (2013.01); *B60T 2210/12* (2013.01)
(58) Field of Classification Search
  CPC ..... G01N 19/02; B60T 2210/12; B60T 8/172; B60T 2210/13; B60W 40/068
  USPC .............................................................. 73/9
  See application file for complete search history.

(56) References Cited

U.S. PATENT DOCUMENTS

| 3,348,784 | A | * | 10/1967 | Gardiner | ................ | B65H 23/18 |
| | | | | | | 242/332 |
| 3,948,080 | A | | 4/1976 | Boyd | | |
| 4,003,241 | A | * | 1/1977 | Thomas | ................. | G01N 19/02 |
| | | | | | | 73/9 |
| 4,315,426 | A | * | 2/1982 | Brandon | ................ | G01N 19/02 |
| | | | | | | 73/146 |
| 4,662,211 | A | * | 5/1987 | Strong | ................... | G01N 19/02 |
| | | | | | | 73/9 |
| 4,779,447 | A | * | 10/1988 | Rath | ...................... | B60T 8/172 |
| | | | | | | 303/150 |
| 5,394,329 | A | * | 2/1995 | Bridgens | ................ | B60T 8/172 |
| | | | | | | 180/197 |

(Continued)

FOREIGN PATENT DOCUMENTS

| CN | 202869946 U | 4/2013 |
| JP | 2013050416 A | 3/2013 |

(Continued)

OTHER PUBLICATIONS

European Patent Office, European Search Report in related application No. EP 15 19 0893, dated Feb. 29, 2016, 8 pages.

*Primary Examiner* — Eric S McCall
*Assistant Examiner* — Mohammed E Keramet-Amircola
(74) *Attorney, Agent, or Firm* — Hunton Andrews Kurth LLP

(57) ABSTRACT

A friction tester is provided which can measure the friction provided by a surface at a slip speed independent to the speed of travel of the friction tester. The friction tester comprises a vehicle which can travel over a surface at a first speed, and a test element which is driven to a second speed, and a measuring device, wherein the second speed is independently controllable; test element is engaged with the surface; and the first and second speeds are different so that the test element slips over the surface with a slip speed.

15 Claims, 2 Drawing Sheets

(56) References Cited

U.S. PATENT DOCUMENTS

| | | | | |
|---|---|---|---|---|
| 5,948,961 | A * | 9/1999 | Asano | B60T 8/172 73/9 |
| 6,192,736 | B1 * | 2/2001 | Clem | B61K 9/08 73/10 |
| 6,276,189 | B1 * | 8/2001 | Hurson | B60T 8/1725 73/146 |
| 6,418,795 | B2 * | 7/2002 | Im | G01N 3/24 73/841 |
| 6,681,614 | B1 * | 1/2004 | Riffe | G01N 19/02 73/8 |
| 2006/0162420 | A1 * | 7/2006 | Pappas | G01N 19/02 73/9 |
| 2009/0310143 | A1 * | 12/2009 | Gardiner | E01C 23/01 356/600 |
| 2014/0060149 | A1 * | 3/2014 | Alhusain | G01N 19/02 73/9 |
| 2014/0082874 | A1 * | 3/2014 | Dias | B60S 1/0818 15/250.12 |
| 2014/0109647 | A1 * | 4/2014 | Faivre | B60T 8/172 73/9 |
| 2014/0202230 | A1 | 7/2014 | Graflind et al. | |
| 2015/0371094 | A1 * | 12/2015 | Gardiner | E01C 23/01 348/148 |

FOREIGN PATENT DOCUMENTS

| | | |
|---|---|---|
| SU | 1567917 A1 | 5/1990 |
| WO | 96/28719 A2 | 9/1996 |
| WO | 00/17024 A1 | 3/2000 |

* cited by examiner

FRICTION TESTER FOR A TRAVEL SURFACE

CROSS-REFERENCE TO RELATED APPLICATION

The present application claims priority to British patent Application No. 1418818.9 field on Oct. 22, 2014, which is incorporated herein by reference in its entirety.

TECHNICAL FIELD

The present invention relates to an apparatus for measuring the friction of a surface.

BACKGROUND

It is desirable to test the friction provided by a road surface, carriageway, runway or the like. A road, runway or other with poor friction is potentially dangerous to users. The friction provided by a surface may change over time, depending on the composition of the surface and the conditions or wear it has been exposed to. The amount of friction provided may vary at corners or near junctions as these areas may be subjected to greater loading by turning, braking or accelerating actions. Friction may also vary across the width of a carriageway. Therefore it is desirable to be able to monitor the frictional properties of a carriageway.

Known friction testers include vehicles with a braked tyre engaged with a surface to be tested.

US 2014/0202230 discloses a friction testing device with a first and second wheel, where the first and second wheels are connected by a transmission so that the first wheel and second wheel rotate at different (but related) speeds of rotation so that, when both wheels are engaged with a surface, one of the wheels slips over the surface.

WO 00/17024 discloses a friction measuring system with a test wheel connected to an electric motor. An accelerating or breaking force is applied to the test wheel to create slippage, and measurements are taken to determine road surface friction.

U.S. Pat. No. 3,948,080 discloses a device to test tyre traction by applying a driving or breaking force to a pneumatic tyre and resolving the resultant forces.

SU 1567917 discloses a test wheel attached to a vehicle. The test wheel can be raised and lowered from the surface of the road. The test wheel is driven in the opposite direction to the direction of travel of the vehicle and the speed of travel of the vehicle, and then is lowered onto the surface.

SUMMARY OF INVENTION

According to a first aspect of the present invention there is provided a friction tester comprising: a vehicle arranged to travel along a surface at a first speed; a test element arranged to engage with the surface; a motor to drive the test element at a second speed; and a measuring device; wherein the second speed is independently controllable with respect to the first speed, the second speed is not equal to the first speed so that the test element slips over the surface at a slip speed, and the measuring device measures a resultant parameter of the test element slipping against the surface, and wherein the second speed is controlled to obtain a nominally constant slip speed independent of the vehicle speed.

The friction provided by a road surface varies with the slip speed of an object moving over the surface. For a fair comparison of different surfaces or different parts of a surface, it would be beneficial to be able to test different parts of the surface using the same slip speed. The friction tester described herein allows the test element to be driven to a slip speed that may be greater than the vehicle speed. Thus there is provided a friction tester comprising a test element arranged to travel over a surface to measure the friction between the surface and the test element, where the test element has a slip speed with respect to the surface which is not related to the vehicle speed by a constant of proportionality.

By having a motor to drive the test element a friction tester is provided which can test surface friction at a slip speed greater than the speed of travel of the testing vehicle. The vehicle can move at low speeds, for example at junctions, or can be stationary at the junction, without affecting the slip speed being used to test the friction of the surface.

According to a second aspect of the invention there is provided a method of testing friction using a friction tester comprising a vehicle and a test element which is engaged with a surface and driven by a motor, the method comprising:
moving the vehicle at a first speed along the surface;
driving the test element to a second speed using the motor, wherein the second speed is different to the first speed so that the test element slips along the surface at a slip speed;
measuring a resultant parameter of the test element slipping over the surface; and comparing the first speed to the second speed and adjusting the test speed using the motor to obtain a nominally constant slip speed.

BRIEF DESCRIPTION OF THE DRAWINGS

For a better understanding of the present invention, and to show more clearly how it may be carried into effect, reference will now be made, by way of non-limiting example, to the following drawings, in which.

DETAILED DESCRIPTION

"Skid resistance" or the "skid resistance level" is a function of the friction provided by a surface. The sliding friction provided by a road when an object is skidding over a surface is of particular importance during heavy deceleration of a vehicle as it determines how far a vehicle, such as a car, will skid on a surface before it stops. The "slip" or "slip speed" of an object over a surface is the relative motion between the object and the surface it is moving on.

Surface friction varies depending on the slip speed of an object travelling over it (as well as on other factors such as how much liquid is on the surface). Friction peaks at a slip speed of around 18 $kmh^{-1}$ on a typical road surface (although this can vary), after which it drops off Previously macro texture has been a good model of how friction drops off/decreases with higher slip speeds. For some new surfaces, however, this model fails. Surfaces can have poor macro texture but may still have acceptable coefficients of friction at higher slip speeds. Therefore a reliable way of directly testing the surface friction at known slip speeds is desirable, rather than relying on the macro texture model.

Previously the speed of skid resistance testing has been limited by the speed of the vehicle, which sometimes has to be slowed down for safety reasons e.g. at corners, junctions etc. In a known friction testing system, a tyre may be held at an inclined angle to the direction of travel. The force acting on the tyre to hold it at that angle may be measured and is indicative of the road surface friction. Such a system is commercially available under the trade name "SCRIM®". An alternative system provides a tyre aligned with the direction of motion but braked or cogged to a slower rotational speed than its free rolling speed. Due to the nature of these surface testing systems, measurements can only be performed on a test element with a slip speed equal to or less than the speed of the vehicle to which it is attached. Thus, if a vehicle slows down for a junction, the coefficient of friction may not be evaluated for a given slip speed.

Figure 1:
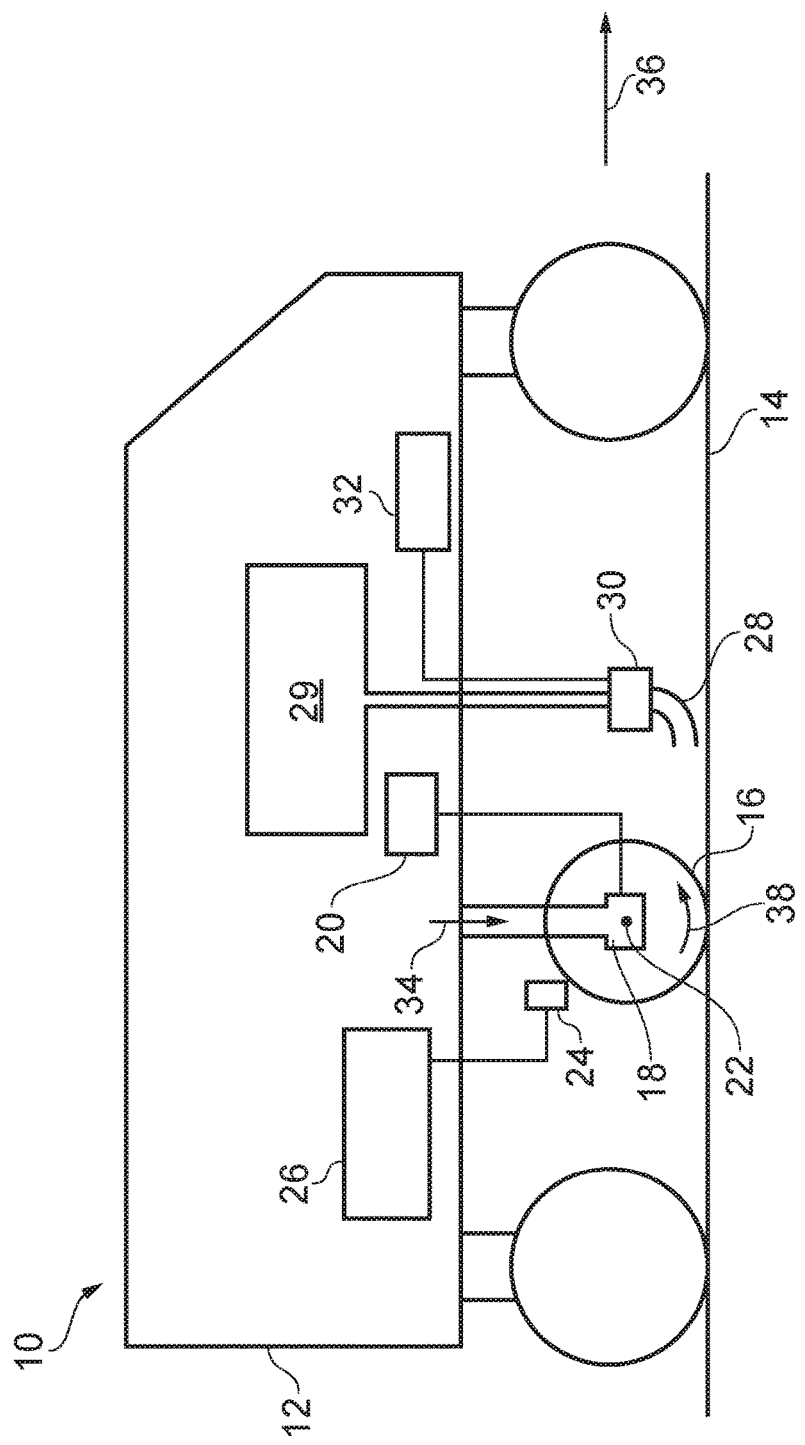
FIG. 1 shows an embodiment of the friction tester.

FIG. 1 schematically shows a friction tester (in which the body parts of a vehicle have been drawn as displaced from the wheels to provide space in the figure to illustrate other components of the tester) suitable for testing the friction provided by a surface and which can make measurements at a nominally constant slip speed even if the vehicle carrying the friction tester travels at a speed slower that the slip speed.

The friction tester 10 comprises a vehicle 12 which can travel along a surface 14. The surface 14 could be a road, carriageway, runway or the like. The vehicle 12 can be any body suitable to travel over such a surface. For example, the vehicle 12 could be a car, van or a lorry, or may be a trailer towed by another vehicle, or a cart that is pushed by a person.

The friction tester 10 further comprises a test element 16 which in the embodiment shown in FIG. 1 is a wheel. The test element 16 is selectively engageable with the surface 14. In FIG. 1, the test element 16 is provided below the body of the vehicle 12. The test element may attached by an arm to the vehicle 12 to allow the lateral position of the test element with respect to the vehicle to be varied, and/or to allow the test element to be lifted out of engagement with the surface when testing is not being performed to travel over the surface.

In other variations the test element may be placed away from the vehicle, for example behind the vehicle, to the side of the vehicle, or in front of the vehicle. Similarly the test element 16 may be any suitable element. For example, the test element may be a caterpillar track, or a body attached by an arm to travel over the surface. Thus if the test element was a pad, the arm may be driven in an oscillatory motion to allow measurements to be taken at a range of test speeds during each oscillation.

Returning to the embodiment shown in FIG. 1, a motor 18 drives the test element 16 to move it at a test speed. The movement of the test element 16 may be in a direction parallel to the direction of travel of the vehicle. The test speed is independently controllable of the vehicle speed. Alternatively the test element, such as a test wheel, may be arranged to rotate obliquely to the direction of travel. The test element may be selectively movable between parallel and oblique positions. This may be advantageous if the surface has a non-homogeneous coefficient of friction, for example because the surface has a texture (such as grooves) which can the effective coefficient of friction to depend upon the direction of movement over the surface.

The motor 18 may be any type of motor. For example, the motor 18 may be a hydraulic motor, an electric motor or an internal combustion engine. The motor may be associated with a variable ratio gear system. Alternatively, the motor 18 may comprise two motors, for example a hydraulic motor and a second motor such as an electric motor to provide fine speed control. The motor may be coupled to a controller 20 which can control the rate at which the motor 18 drives the test element 16. Alternatively the controller 20 may be part of the motor 18. The motor 18 is independently controllable of a propulsion system driving the vehicle to the vehicle speed.

If the test element is a wheel, it is, in use, rotated by the motor 18 around an axis of rotation 22. The axis of rotation 22 of the test element 16 is preferably fixed in relation to a longitudinal axis or direction of travel of the vehicle 12, but as noted above the test wheel may also be oblique to the direction of travel. The axis of rotation is advantageously perpendicular to the direction of travel of the vehicle so the direction of rotation of the test element is parallel to the direction of travel of the vehicle. The motor 18, in use, rotates the test wheel to result in a test speed of the test element, which is the rotation rate (number of rotations per unit time) multiplied by the circumference of the wheel.

A measuring device 24 measures a resultant parameter of movement of the test element 16. The measuring device 24 may measure a resultant force acting on the test element 16, for example by measuring the drive torque provided to the test wheel or by measuring a force acting at a support for the wheel. Where a test wheel is at an oblique angle to the direction of travel, the force or torque that acts to turn it to align with the direction of travel may be measured in order to estimate the friction of the surface. The contact force between the wheel and the road may be measured and may also be adjustable in order to determine the coefficient of friction and/or to control the torque/power demanded from the motor or energy dissipated at the test element. The measuring device 24 provides data to a data capture system 26. The data capture system 26 may include or be linked to data storage means and data processor. The data storage means may comprise non-volatile memory. The data processor means may further comprise non-volatile program memory and software for collecting and processing the data from the data capturing system and/or the data memory.

It is possible to operate a friction tester without a liquid delivery system. However, although it is possible to test the friction provided by a surface when dry, it is usual to test the friction of a surface when wet. Having liquid on a surface reduces the friction provided by that surface and replicates road performance during rain etc. One standard for testing requires a certain depth of water to be on the surface 14 during the testing. A liquid delivery system 28 is arranged to deliver liquid to the road surface at a delivery region just in front of the test element 16. Preferably the liquid is water. The liquid delivery system may comprise a tank 29, a delivery pipe and a valve or pump 30 linked to a controller 32. The rate of delivery of the liquid can be controlled by the valve or a pump, 30, which is responsive to the controller 32.

Means, such as weights, springs or actuators are provided to urge the test element 16 against the surface 14. A load is denoted by arrow 34. The load is known, either through applying a pre-measured load or through measuring the force urging the test element into engagement with the surface.

The vehicle 12 can, in use, travel along the surface 14 at a vehicle speed indicated by arrow 36. During operation the vehicle travels along the surface 14 thereby being able to test various parts of the surface, including the surface at road junctions. The vehicle speed can be measured using a transducer co-operating with a wheel of the vehicle or a prop shaft of the vehicle, or could be picked up from the vehicle's ABS system, or may be provided by a separate speed measurement system which may, for example, be GPS based.

When the friction tester 10 is in operation, the vehicle 12 travels along the surface 14 at a vehicle speed 36. The test element 16 which engages with the surface 14 is driven by the motor 18 such that the test element has a test speed 38. The motor 18 is controlled by controller 20 so that the test speed 38 is different to the vehicle speed 36 and can be greater than the vehicle speed. Since the test element 16 is attached in fixed relationship to the vehicle 12, the test element 16 cannot move over the surface 14 at its test speed 38. Instead, the test element slips (skids) over the surface 14. The test element slips over the surface at a slip speed (the relative motion between the edge of the test element and the surface) which is equal to the difference in the vehicle speed 36 and the test speed 38.

The slip of the test element 16 over the surface 14 results in a resultant force acting on the test element, which is caused by the friction between the test element and the surface. The resultant force can be measured and used to calculate the surface friction.

The measuring means, such as a torque sensor or a load sensor, 24 measures the resultant force resulting from the inter-engagement between the test element and the road. The resultant force depends on many factors, including: the skid resistance of the surface, the load 34 applied to the test element 16 to urge the test element against the surface, and the slip speed of the test means over the surface 14. The measuring means 24 supplies measured data to the data capture system 26. The measured data is stored along with data relating to the above factors: the test speed 38, the vehicle speed 36, and the load 34. This combined data can then be used in calculations to work out the friction provided by the surface. The data can be stored and the calculation performed at a later time, or the calculation can be done in real time.

The liquid delivery system 30 supplies liquid (usually water) to the surface just in front of the test element 16. The flow controller 32 sets the control valve or pump 30 to deliver the liquid at a flow rate based on the vehicle speed 36, and the test speed 38. Usually for surface testing a minimum depth of water is required to be present on the surface. The controller 32 and valve or pump 30 can ensure that this minimum depth is maintained.

As the vehicle 12 moves forward at the vehicle speed 36, the test element 16 also moves forward at the vehicle speed 38. Therefore the surface beneath the test element will be constantly changing, and the liquid delivery system 28 supplies the surface with water in order to wet the new areas of the surface about to come into contact with the test element 16. The rate of liquid delivery should therefore depend on vehicle speed (the faster the vehicle speed, the larger the amount of surface passing beneath the test element, the more liquid is needed to be supplied to maintain the minimum depth of liquid on the surface). The water flow rate may, for example, be generally proportional to the vehicle speed.

Further, as the test element 16 rotates it may push away some of the liquid on the surface 14. If the test element 16 has a test speed of much higher than the vehicle speed, then the test element will be "pushing" liquid away from the surface beneath it at a faster rate than the liquid is being supplied. Therefore it is advantageous for the liquid delivery rate to depend on the test speed of the test element 16.

It is further possible to operate the friction tester with a vehicle speed of zero. In this case the flow rate may depend only upon the test speed 38 of the test element 16. When the vehicle is stationary the test element will not be moving over the surface onto new areas, and therefore it is not as necessary to wet the surface in front of the test element 16. Instead, the liquid delivery needs to be provided as close as possible to the area of engagement between the test element and the surface.

Therefore a system is provided which can test the surface friction at a slip speed independent to the vehicle speed. The slip speed may be higher than the vehicle speed, or the slip speed may be controlled to a desired slip speed at which to test all, or some, of the surface.

Figure 2:
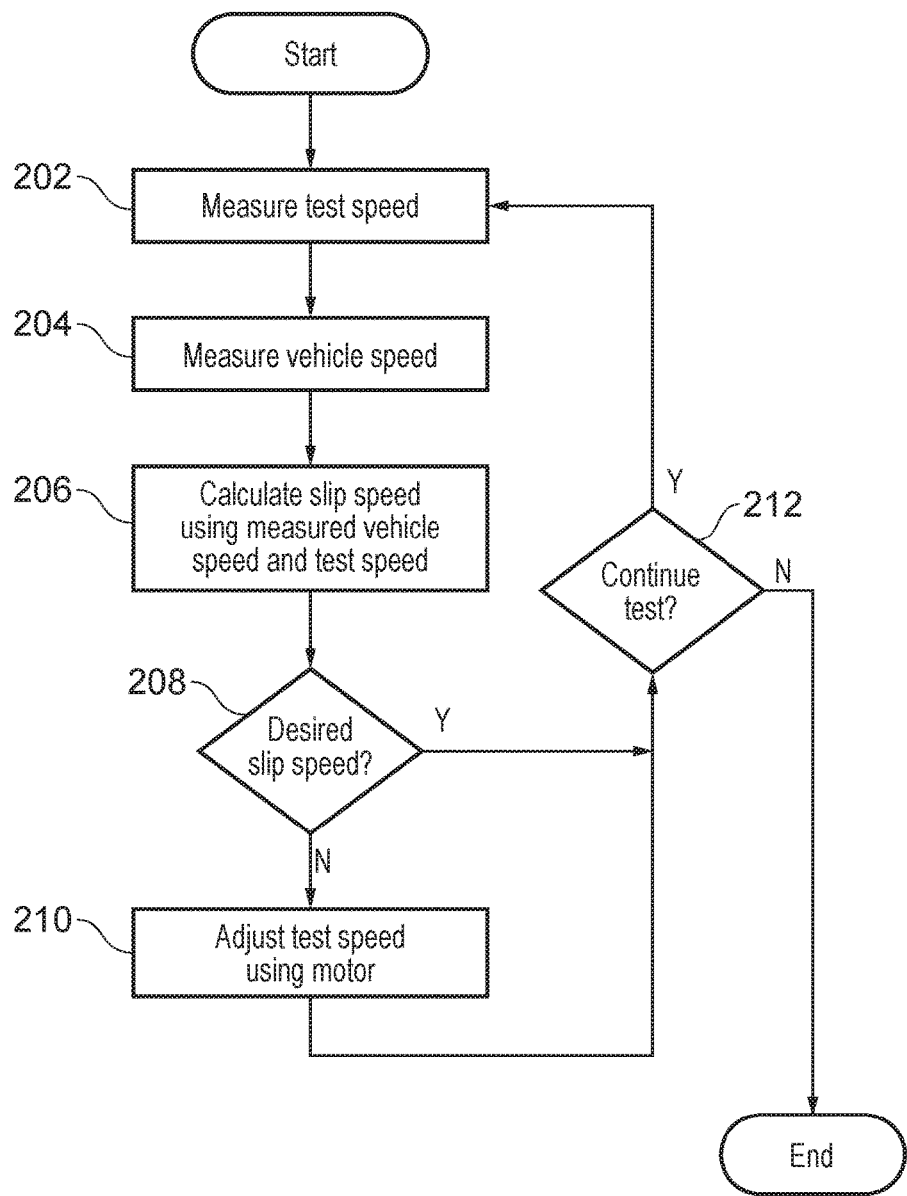
FIG. 2 shows a flow diagram for achieving a desired slip speed of the test element.

FIG. 2 shows a flow diagram of the controller 20 for adjusting the slip speed of the test element to ensure it has a desired slip speed. The vehicle 12 travels with a vehicle speed 36 and the test element 16 is driven by the motor 18 at test speed 38. In step 202 the controller 20 measures the test speed 38, i.e. the circumpherential speed of the test wheel. This could either be through calculation of the test speed using information from the driving means (how quickly the motor is driving the test element). The controller 20 then, in step 204, measures the vehicle speed 36. As explained previously, this could be done through using a transducer co-operating with a wheel or a prop shaft of the vehicle, or using the vehicle's ABS system, or a separate speed measurement system (e.g. GPS).

The controller 20 then, in step 206, calculates the slip speed of the test element using the test speed and vehicle speed as measured in steps 202 and 204 respectively. The slip speed of the test element will usually be the difference between the vehicle speed and the test speed.

In step 208, the calculated slip speed is compared to a desired slip speed known by the controller. The desired slip speed could be manually entered into a computer system associated with a controller, or could be stored in a database or the like. If the calculated slip speed is equal to the desired slip speed, then no immediate action needs to be taken and the process continues to step 212.

If the calculated slip speed is not equal to the desired slip speed then the controller 20, in step 210, adjusts the speed of the test element using the motor 18. The motor could be controlled to drive the test element to a faster speed, or to a slower speed. The process then continues to step 212.

In step 212 the controller 20 checks whether the test should continue. If the test should continue, then the process returns to step 202. If the test should not continue, then the process ends.

It is important to note that the steps described in the above process could be done in many different orders. For example, the vehicle speed could be measured before the test speed is measured. The controller can continue adjusting the test speed until the desired slip speed is reached. The desired slip speed could be changed at any point, either through programming or through a manual input. The controller continues monitoring the slip speed and adjusting the test speed to obtain the desired slip speed, until the test comes to an end.

The process can be demonstrated using the following example, wherein the desired slip speed is 20 kmh$^{-1}$, and the surface of a T-junction is to be tested. In order to do this, the vehicle travels to the T-junction with a vehicle speed 36 and the test element 16 is driven by the motor 18. Whilst the vehicle is travelling the test element is driven at a test speed such that the slip speed of the test element is 20 kmh$^{-1}$, which takes into account the vehicle speed 36. On reaching a "Give Way" sign at the T-junction the vehicle must stop. When the vehicle speed is zero, the test element is driven such that the test speed (and the skid speed) is 20 kmh$^{-1}$, hence testing the surface friction at the desired 20 kmh$^{-1}$. When the road is clear and the vehicle can move off through the junction, the motor 18 changes the test speed 38 to maintain a slip speed of 20 kmh$^{-1}$ whilst taking into account the vehicle speed 36 as it accelerates from stationary. In this way, any area of a road surface can be measured at any desired slip speed, without endangering road safety.

The test element can be driven in a direction opposite to the direction of travel in order to obtain even higher slip speeds (in this case the slip speed would be the sum of the test speed and the vehicle speed). Alternatively, the test element could be moved in a direction different to the direction of travel of the vehicle. In this case, the slip speed could be calculated using vectors of the test velocity and the vehicle velocity.

Therefore, a friction tester is provided which can measure the friction provided by a surface at a slip speed which is independent to the speed of travel of the friction tester. The slip speed could be greater than the speed of travel of the friction tester, or maintained at a desired slip speed regardless of the speed of the vehicle, in order to make comparable measurements across different areas.

By being able to drive the wheel in the direction of travel, and also opposite to the direction of travel, friction can be tested in different directions for the same bit of road surface. This may indicate asymmetric wear of the surface and different performance under break and acceleration conditions.

Multiple test wheels may be carried on the same test vehicle to obtain a plurality of slip speed measurements during a single measurement pass of the vehicle over the road or other surface.

Those skilled in the art will appreciate that various amendments and alterations can be made to the embodiments described above without departing from the scope of the invention as defined in the claims.

The invention claimed is:

1. A friction tester comprising:
   a vehicle arranged to travel along a surface at a first speed;
   a test element arranged to engage with the surface;
   a motor to drive the test element at a second speed; and
   a measuring device;
   wherein:
   the second speed is independently controllable of the first speed;
   the second speed is not equal to the first speed so that the test element slips over the surface at a slip speed; and
   the measuring device measures a resultant parameter of the test element slipping against the surface and wherein the second speed is controlled to obtain a nominally constant slip speed independent of the vehicle speed.

2. A friction tester according to claim 1, wherein the second speed is greater than the first speed when the first speed is less than a desired slip speed.

3. A friction tester according to claim 1, further comprising a load to drive the test element into the surface.

4. A friction tester according to claim 1, wherein the slip speed is equal to the difference in the first speed and the second speed.

5. A friction tester according to claim 1, wherein friction properties of the surface can be calculated using data from the measuring device, as a function of the first and/or second speeds.

6. A friction tester according to claim 3, wherein the friction properties of the surface can be calculated as a function of the load on the test element.

7. A friction tester according to claim 1, wherein the motor is a hydraulic motor, an electric motor or a combination of motors acting together.

8. A friction tester according to claim 1, wherein the resultant parameter is a force acting on the test element.

9. A friction tester according to claim 1, wherein the test element is a wheel.

10. A friction tester according to claim 1, further comprising a liquid delivery system for wetting the surface in front of the test element.

11. A friction tester according to claim 10, wherein the rate of delivery of the liquid is a function of the first speed and/or the second speed.

12. A friction tester according to claims 10, wherein the rate of delivery of the liquid is substantially proportional to the first speed and/or the second speed.

13. A friction tester as claimed in claim 1, comprising a plurality of test elements driven to respective slip speeds.

14. A friction tester as claimed in claim 1, in which the motor can drive the test element in a forward direction and/or in a backward direction.

15. A method of testing friction using a friction tester comprising a vehicle and a test element which is engaged with a surface and driven by a motor, the method comprising:
   moving the vehicle at a first speed along the surface;
   driving the test element to a second speed using the motor, wherein the second speed is independently controllable of the first speed, the second speed is not equal to the first speed so that the test element slips along the surface at a slip speed; and
   measuring a resultant parameter of the test element slipping over the surface, the method further comprising comparing the first speed to the second speed and adjusting the test speed using the motor to obtain a nominally constant slip speed.

* * * * *